United States Patent [19]
Ulmer et al.

[11] Patent Number: 5,994,385
[45] Date of Patent: Nov. 30, 1999

[54] PERSONAL CARE PRODUCT INCLUDING A DERIVATIZED POLYMER OF MALEIC ANHYDRIDE ALKYL HALF-ESTER OR FULL ACID, MALEAMIC ACID AND MALEIMIDE UNITS

[75] Inventors: Herbert W. Ulmer, Hoboken; John A. Katirgis, West Caldwell; Timothy Gillece, Pompton Plains, all of N.J.

[73] Assignee: ISP Investments Inc., Wilmington, Del.

[21] Appl. No.: 09/191,736

[22] Filed: Nov. 13, 1998

Related U.S. Application Data

[60] Division of application No. 09/104,309, filed as application No. PCT/US98/04240, Mar. 4, 1998, which is a continuation-in-part of application No. 08/845,669, Apr. 25, 1997, Pat. No. 5,869,695.

[51] Int. Cl.$^6$ .......................... A61R 31/415; A61R 31/74; A01J 21/00; A01J 25/12
[52] U.S. Cl. .......................... 514/397; 424/78.02; 424/401
[58] Field of Search ..................................... 548/545, 546, 548/547; 514/397; 424/401, 78.02

[56] References Cited

U.S. PATENT DOCUMENTS

| 2,262,262 | 11/1941 | Speer .................................. 548/545 X |
| 4,839,072 | 6/1989 | Gutierrez et al. .................... 548/545 X |
| 4,841,069 | 6/1989 | Olsen ...................................... 548/545 |
| 5,554,768 | 9/1996 | Donges et al. ......................... 548/545 |
| 5,869,695 | 2/1999 | Ulmer et al. ............................ 548/545 |

FOREIGN PATENT DOCUMENTS 0545202  8/1957  Canada .

Primary Examiner—Floyd D. Higel
Attorney, Agent, or Firm—Walter Katz; William J. Davis; Marilyn J. Maue

[57] ABSTRACT

A process for making derivatized polymers of maleic anhydride containing maleamic acid and its corresponding cyclic imide repeat units, in alcohol solution, at a temperature of about 60–160° C., during a reaction period of about 1–25 hours. The product is a polymer having a predetermined ratio of the above repeat units. The polymers are included in personal care poducts.

8 Claims, 3 Drawing Sheets

PERSONAL CARE PRODUCT INCLUDING A DERIVATIZED POLYMER OF MALEIC ANHYDRIDE ALKYL HALF-ESTER OR FULL ACID, MALEAMIC ACID AND MALEIMIDE UNITS

CROSS-REFERENCE TO COPENDING U.S. PATENT APPLICATIONS

This application is a division of U.S. Ser. No. 09/104,309, filed Jun. 24, 1998 allowed and final fee paid Mar. 30, 1999 which is a continuation-in-part of U.S. patent application Ser. No. 08/845,669, filed Apr. 25, 1997, now U.S. Pat. No. 5,869,695, and assigned to the same assignee as herein said Ser. No. 09/104,309 is a 371 of PCT/US98/04240, filed Mar. 4, 1998.

BACKGROUND OF THE INVENTION

1. Field of the Invention

This invention relates to polymers of maleic anhydride, and, more particularly, to a process of making derivatized maleic anhydride polymers which include maleamic acid and/or its cyclic imide repeat units.

2. Description of the Prior Art

Amines can be reacted with maleic anhydride to give the corresponding half-amide derivative. Generally, a polymer containing maleic anhydride is reacted in solution or suspension with an amine in an inert or non-reactive solvent, such as acetone, heptane, benzene or dibutylether, to provide the desired half-amide derivative. This material then must be isolated and repackaged into a useful product.

Unfortunately, various side reactions occur during such solution or suspension processes. These side reactions adversely affect the quality of the final product, particularly its color and odor. The amine reactant also can form a salt with the half-acid polymer instead of reacting with the anhydride and reduce the yield of the desired amide reaction product.

The reaction of amines with anhydride polymers in an inert solvent also is difficult to control because of its rapid reaction rate and high reaction exotherm leading to the formation of a non-homogeneous reaction product.

Reactions of anhydride polymers with amines in inert solvents present other problems, too. For example, if the reaction is conducted as a slurry, e.g. reaction of p(methyl vinyl ether-maleic anhydride copolymer) with an amine in toluene, the consistency of the slurry may change as the amine reacts with the anhydride polymer. This consistency change usually results in excessive swelling of the polymer during the reaction, which can make subsequent processing very difficult unless the slurry is sufficiently diluted with solvent. However dilution reduces polymer capacity. Reaction of the anhydride polymer as a solution in an inert solvent such as acetone with amine is advantageous but it may result in considerable gelling or precipitation of the reaction product or the formation of "fish eyes".

Similar reactions of anhydride polymers with amines in a reactive solvent such as ethanol may solve these problems because the resultant products are generally made available in the form of homogeneous solution or stable colloidal suspensions which are easy to handle even at a high solids content.

Accordingly, it is an object of this invention to provide a new and improved process of making derivatized maleic anhydride polymers, and, particularly, to a process of making substantially homogeneous maleic anhydride-containing polymers which include maleamic acid and its cyclic imide derivatives.

Another object herein is to provide a process of making polymers containing a maleic anhydride, and its maleamic acid and corresponding cyclic imide derivatives, in a predetermined ratio of each.

A feature of the invention is the provision of such process which is carried out in an alcohol as a reactive solvent.

Another feature of the invention is to control the reaction temperature and period of reaction during the process to predetermine the ratio of each of the maleic anhydride-half-ester, maleamic acid and cyclic imide repeat units of the polymer obtained.

Yet another feature herein is to provide a derivatizing reaction which can be carried forward substantially to completion with little or no unwanted side reactions.

Yet another feature is a derivatization reaction which does not need an esterification or acidification catalyst, and is conducted in a non-toxic solvent.

Among the other features of the invention is the provision of a terpolymer product having little color or odor and little free amine.

These and other objects and features of the invention will be made apparent from the following detailed description of the invention.

SUMMARY OF THE INVENTION

What is described herein is a process of forming a polymer which includes the following repeat units:

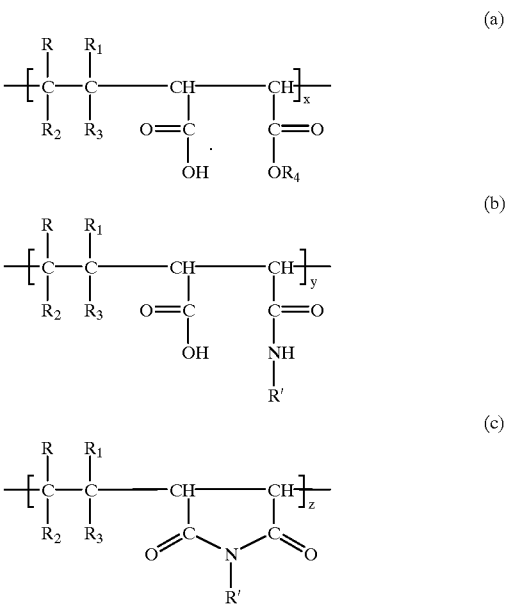

where R, $R_1$, $R_2$ and $R_3$ form a straight chain or cyclic amido group, and $R_4$ is alkyl;

R' is hydrogen, aryl, alkyl or alkyl derivatized with fluoro, silyl, amino or olefinic; and x is 0.05–0.95, y=0–0.90 and z=0.05–0.95; which comprises reacting:

(d) 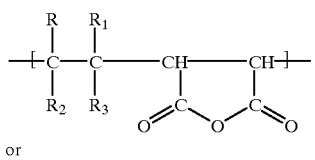

or (d) 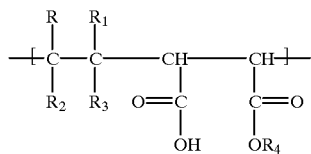

in alcohol solution, $R_4OH$,
where R, $R_1$, $R_2$ and $R_3$, and $R_4$ are as defined above, with an α-unsubstituted primary amine, $R'NH_2$, where R' is as defined above, at a temperature of about 60–160° C., for a predetermined period of time.

In the preferred embodiments of the invention, the reaction temperature is about 80–150° C., most preferably about 100–120° C., and the reaction time is about 1–25 hours, most preferably about 2–10 hours.

Preferred starting copolymers include an acrylamido or methacrylamido, a vinylpyrrolidone or vinyl caprolactam-maleic anhydride copolymer, or their corresponding half-esters.

The preferred α-unsubstituted amines are $C_1$ to $C_{40}$ alkyl α-unsubstituted primary amines, such as n-hexylamine, n-octylamine, and 2-ethylhexylamine. Ammonia, silated primary amines, fluorinated primary amines, halogenated primary amines, unsaturated amines, cyano amines and amphoteric amines also may be used.

In one embodiment of the invention, a polymer having no amide component, i.e. no remaining amide resulting from the reaction of amine and maleic anhydride, can be obtained by carrying out the process at 115° C. for 5 hours or longer. The resultant polymer thus includes only half-ester and cyclic imide repeat units therein.

IN THE DRAWINGS

FIG. 1 is a plot of unreacted amine vs. reaction time to show the effect of reaction temperature on the course of the derivation reaction.

FIGS. 2A, 2B, 2C, and 2D are plots of mole % of each repeat unit in the resultant polymer vs. reaction times, at different reaction temperatures.

DETAILED DESCRIPTION OF THE INVENTION

To illustrate this invention, a maleic anhydride (MAn) copolymer in alcohol solution is derivatized with an α-unsubstituted primary amine to form a polymer containing repeat units of the MAn half-ester, its half-amide, and its corresponding cyclic imide. The reaction is carried out at a predetermined temperature and for a predetermined period of time to provide a polymer having a desired ratio of the above repeat units therein.

A suitable starting material for this process is acrylamido (AA) or methacrylamido (MAA), or vinylpyrrolidone (VP) or vinyl caprolactam (VCL) maleic anhydride copolymer which can be obtained by reaction of MAn and amide to form a powder or solution of the copolymer in solvent. Solutions in which the solvent is a low boiling solvent e.g. acetone, tetrahydrofuran are particularly advantageous, because the solvent can be easily removed by solvent-exchange with added ethanol (or higher alcohol). Then a suitable amine reactant is added to the copolymer-ethanol solution in a predetermined amount to form a reaction mixture containing ethanol as a reactive solvent therein. In the presence of ethanol, the MAn polymer exists therein in equilibrium with its corresponding alkyl half-ester, as shown by the equation below:

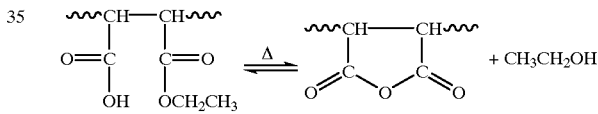

Upon heating this equilibrium reaction mixture to the desired reaction temperature, elimination of alcohol occurs forming the anhydride intermediate. At this point, the added amine reactant can react with the anhydride intermediate to produce the maleamic acid derivative and its cyclic imide. A summary of the reactions involved in the process, and the resultant terpolymer and its repeat units, is shown below:

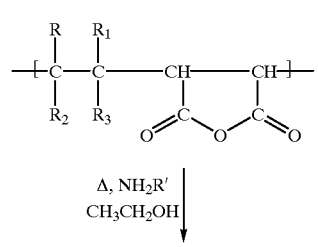 or 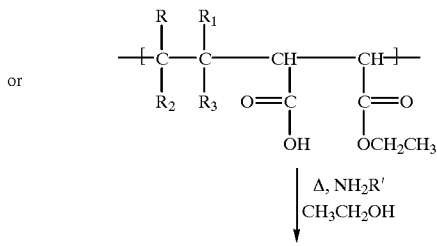

-continued

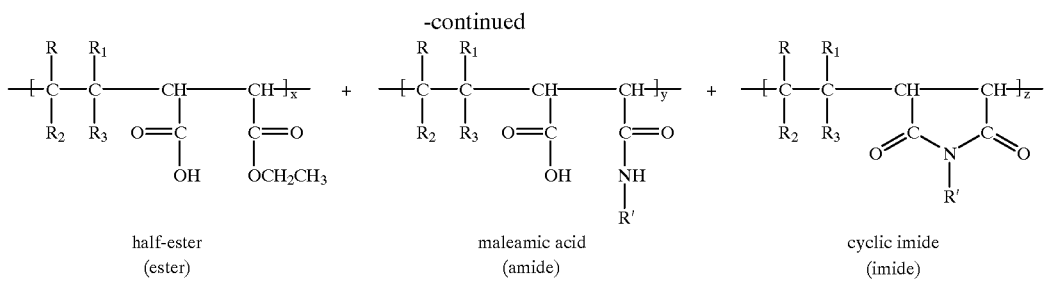

half-ester (ester)   maleamic acid (amide)   cyclic imide (imide)

In general, higher reaction temperatures and longer reaction times enhanced the conversion of amide by loss of a water molecule into the corresponding cyclic imide repeating unit.

Figure 1:
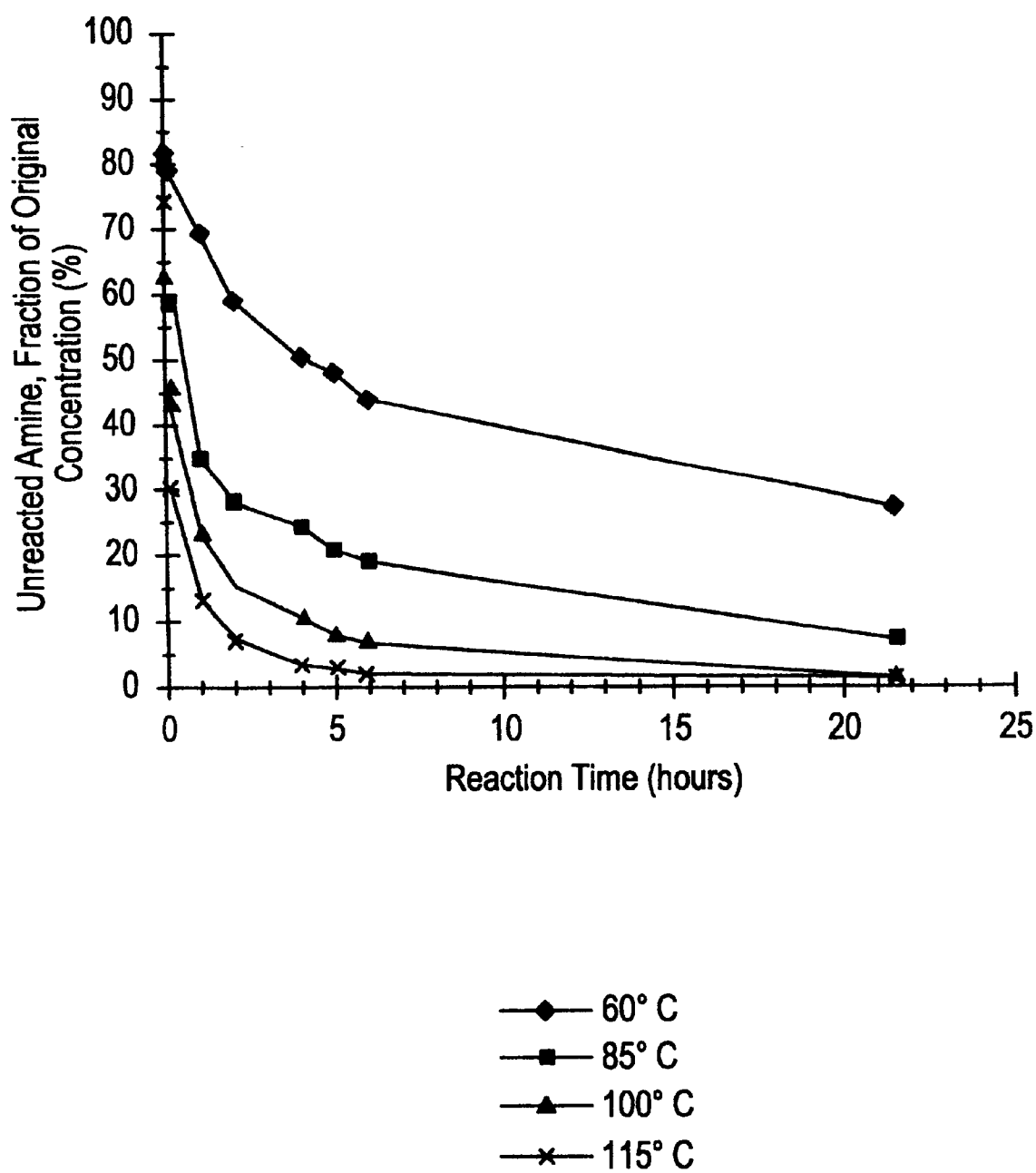
Figure 2A:
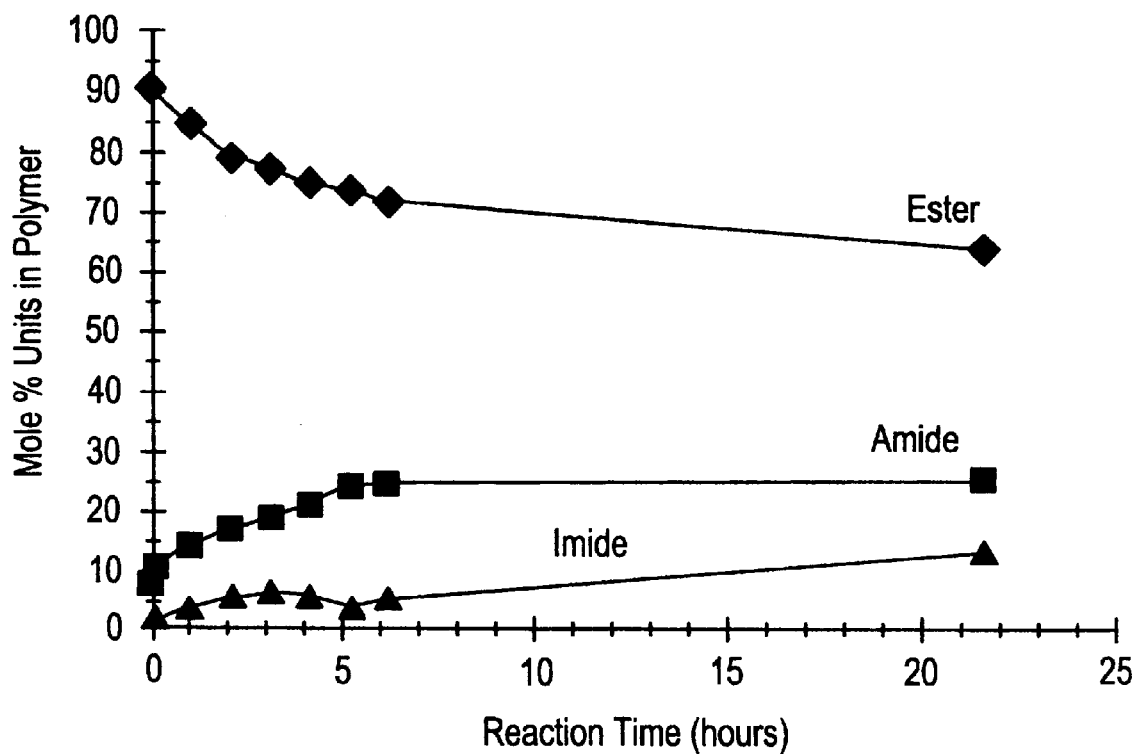
Figure 2B:
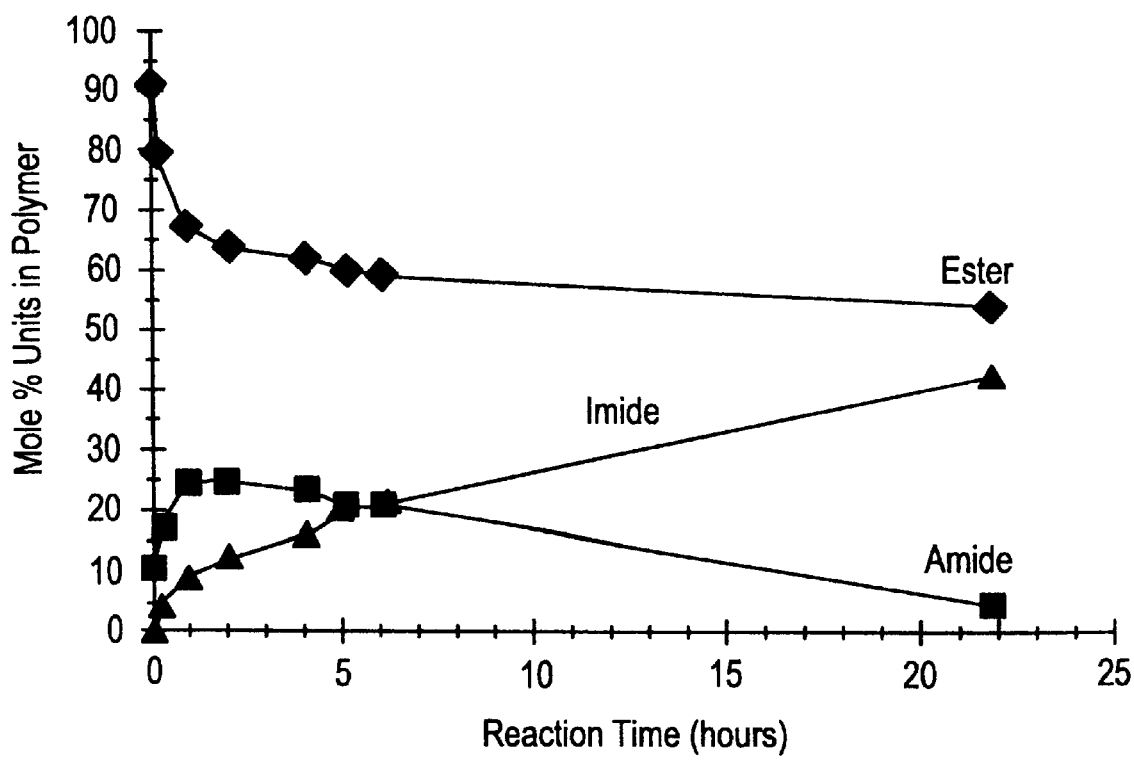
Figure 2C:
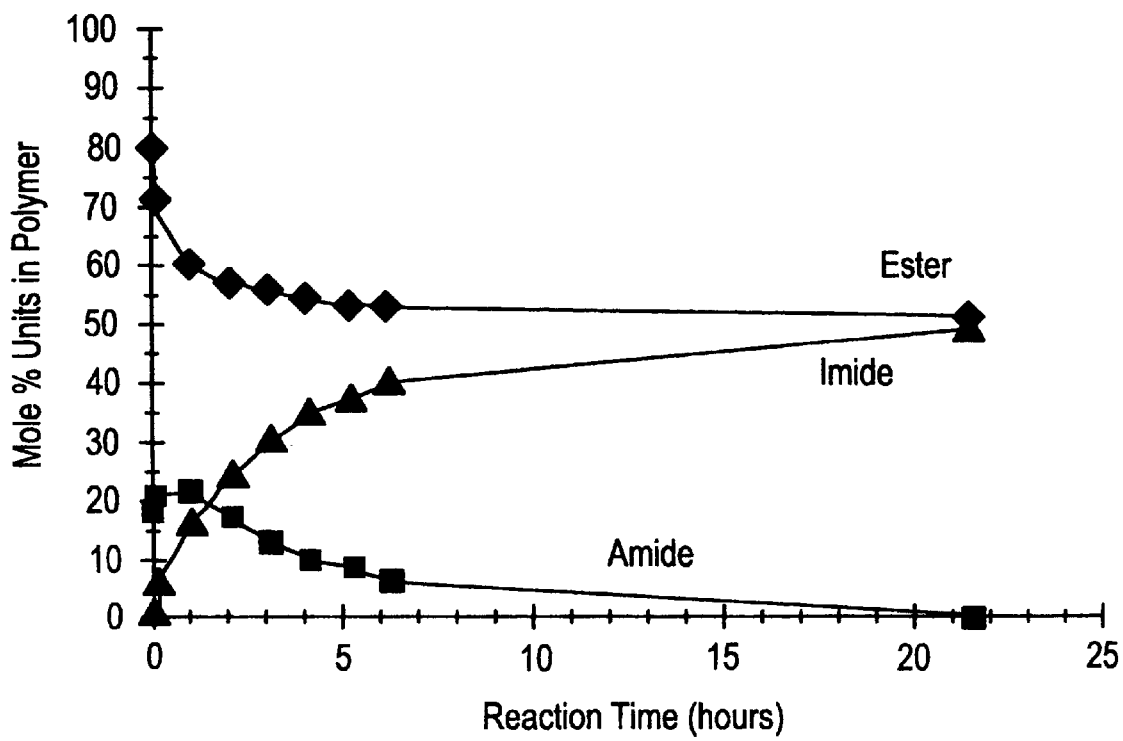
Figure 2D:
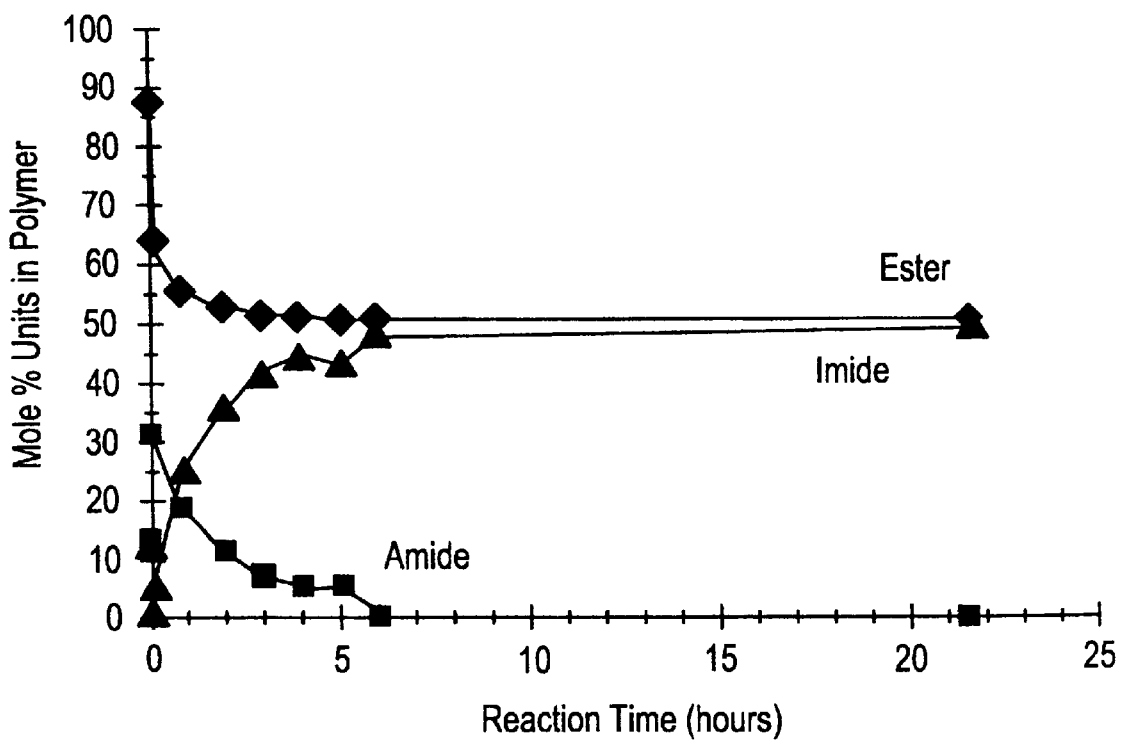

FIG. 1 is a graphical illustration of the course of the reaction of starting copolymer and amine in ethanol solution at various reaction temperatures, plotted as the percent unreacted amine vs. reaction time. These results show that the reaction is strongly temperature dependent. For example, at 60° C., after over 20 hours, almost 30% of the amine reactant remains, while at 115° C., the reaction is substantially complete after only 5 hours.

FIG. 2 shows the effect of reaction temperature and reaction times upon the ratio of each repeat unit in the polymer obtained by the process of the invention. Higher reaction temperatures and reaction periods favor an increased amount of imide over amide repeat units in this polymer, while the ester repeat unit approaches about 50%.

EXAMPLE 1

Acrylamide, AA, maleic anhydride, MAn, anhydride copolymer is diluted with ethanol to give a 30% solids mixture, and to this mixture 50 mole % hexylamine reactant is added. The reaction mixture is purged with $N_2$ gas, heated to 85° C. and held for 20 hours. A resultant terpolymer solution is obtained which is yellow-brown in color with an Acid No. of 149 mg KOH/g polymer and less than 2 wt. % free amine.

EXAMPLE 2

The procedure of Example 1 is followed using methacrylamide (MAA)-maleic anhydride half-ester copolymer in ethanol as starting material, which is diluted with ethanol to give a 30% solids solution. Then 50 mole % n-octylamine is added and the reaction mixture is purged with $N_2$ gas. The reactor is heated to 85° C. and held for approximately 20 hours. The resultant terpolymer solution is brownish in color with an Acid No. of 156 mg KOH/g polymer and less than 3 wt. % free amine present.

EXAMPLE 3

The procedure of Example 1 is followed using vinylpyrrolidone-maleic anhydride copolymer as starting material. The resultant terpolymer product is brownish in color with an acid No. of 130 mg KOH/g polymer.

EXAMPLE 4

The procedure of Example 1 is followed using vinyl caprolactam-maleic anhydride copolymer as starting material. The resultant copolymer is brownish in color with an acid No. of 120 mg KOH/g polymer.

EXAMPLE 5

The following graphs (FIGS. 1 and 2) show the effect of temperature on the incorporation of α-unsubstituted amines into the derivatized copolymer. The reactions are conducted at varying temperatures with 50 mole % 2-ethylhexylamine as reactant. As can be seen from FIG. 1, minimal salt formation is produced at a reaction temperature of 115° C. after only 5 hours of reaction time.* Similar trends are observed with other α-unsubstituted primary amines. Any unreacted amine results in the formation of salt.

As shown in FIG. 2 below, which represent the polymer composition of MAn half-ethyl ester copolymers reacted with 50 mole % of 2-ethylhexylamine, the amide:cyclic imide ratio present in the polymer is largely controlled by the temperature and reaction time conditions. More particularly, an increase in the reaction temperature and an increase in reaction time enhances imide formation over the amide structure in the polymer obtained. In fact, as shown in FIG. 2, at 115° C. and after 5 hours reaction time, the amine reactant, which has been taken up as the amide in the terpolymer, has been converted completely to the cyclic imide form, without requiring removal of water.

The polymers of this invention are particularly useful in personal care and pharmaceutical products such as hair care and skin care products.

While the invention has been described with particular reference to certain embodiments thereof, it will be understood that changes and modifications may be made which are within the skill of the art. Accordingly, it is intended to be bound only by the following claims, in which:

What is claimed is:

1. A personal care product consisting essentially of the polymer made up of the following repeat units:

(a)

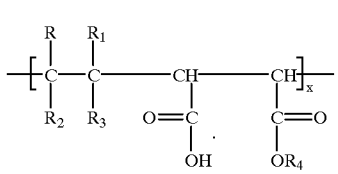

(b)

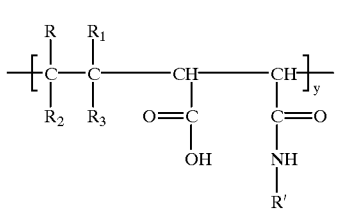

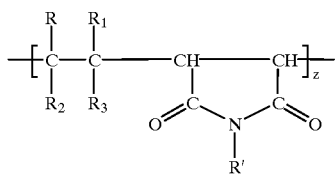 (c)

where R, $R_1$, $R_2$ and $R_3$ form an acrylamido, methacrylamido, vinylpyrrolidone or vinyl caprolactam group; and $R_4$ is alkyl;

R' is hydrogen, aryl, alkyl or alkyl substituted by fluoro, silyl or amino; and x is 0.05–0.95, y=0–0.90 and z=0.05–0.95.

2. A personal care product according to claim 1 which is a hair care product.

3. A personal care product according to claim 1 which is a skin care product.

4. A personal care product according to claim 1 wherein $R_1$, $R_2$, $R_3$ and $R_4$ form an acrylamido or methacrylamido group.

5. A personal care product according to claim 1 wherein $R_1$, $R_2$, $R_3$ and $R_4$ form a vinylpyrrolidone group.

6. A personal care product according to claim 1 wherein $R_1$, $R_2$, $R_3$ and $R_4$ form a vinyl caprolactam group.

7. A personal care product according to claim 1 wherein

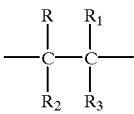

is acrylamide.

8. A personal care product according to claim 1 wherein

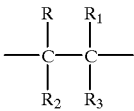

is methacrylamide.

* * * * *